United States Patent [19]
Williams et al.

[11] Patent Number: 5,124,797
[45] Date of Patent: Jun. 23, 1992

[54] MODULAR VIEW LENS ATTACHMENT FOR MICRO VIDEO IMAGING CAMERA

[75] Inventors: P. Michael Williams, San Carlos; Ronald R. Williams, Placerville; Steven M. Mortensen, Redwood City, all of Calif.

[73] Assignee: New Image Industries, Inc., Canoga Park, Calif.

[21] Appl. No.: 556,557

[22] Filed: Jul. 20, 1990

[51] Int. Cl.$^5$ .......................... H04N 5/225; H04N 7/18
[52] U.S. Cl. ........................ 358/225; 358/98; 358/93; 433/29
[58] Field of Search ............... 358/225, 229, 98, 100, 358/901, 99, 93; 128/6, 4; 433/29, 31

[56] References Cited

U.S. PATENT DOCUMENTS

| | | | |
|---|---|---|---|
| 4,589,404 | 5/1986 | Barath | 358/98 |
| 4,600,939 | 7/1986 | Sluyter | 358/98 |
| 4,639,772 | 1/1987 | Sluyter | 358/98 |
| 4,722,000 | 1/1988 | Chatenever | 358/98 |
| 4,837,615 | 6/1989 | Boshier | 358/100 |
| 4,858,001 | 8/1989 | Milbank | 358/225 |
| 4,915,626 | 4/1990 | Lemmey | 358/225 |
| 4,919,114 | 4/1990 | Miyazaki | 358/98 |

Primary Examiner—Howard W. Britton
Assistant Examiner—Sherrie Hsia
Attorney, Agent, or Firm—Marvin H. Kleinberg

[57] ABSTRACT

A micro video imaging camera has a detachable distal module which is replaceable with one of different characteristics (e.g., angled), and sterilizable. Thus a non-replaceable CCD and video transmitter are connected to an inner body which comprises in effect a lens tube. The module comprises an outer body encasing the inner body which has a filter (optional) at its tip and a magnifying lens optically connected to an image conduit optical segment. The inner body receives the image conduit, the output of which is focused by the lens in the inner body on a CCD microprocessor. The model may be replaced with an angular distal end or lenses of different fields of view. Fiber optic light filaments may be used to illuminate the field of view of the tip of the module, either housed internally or externally of the inner body.

2 Claims, 3 Drawing Sheets

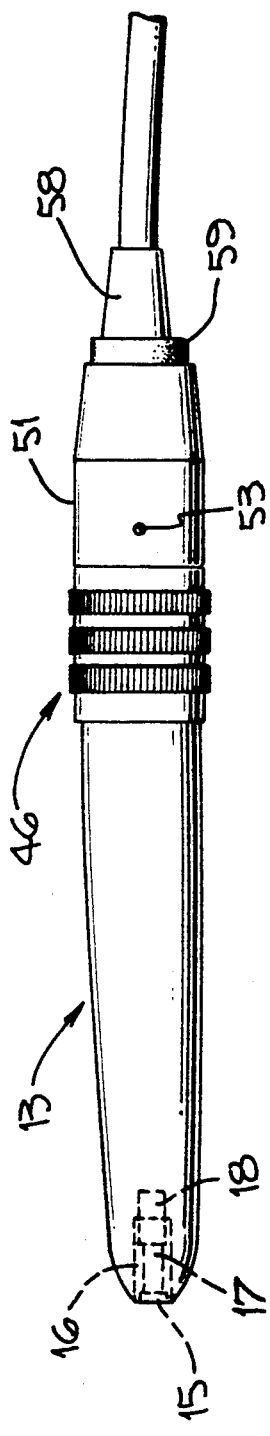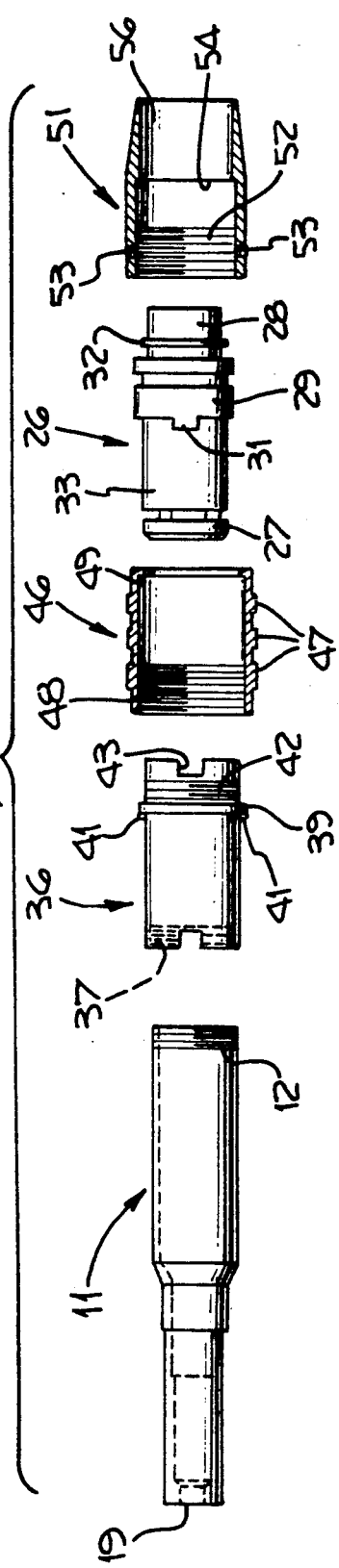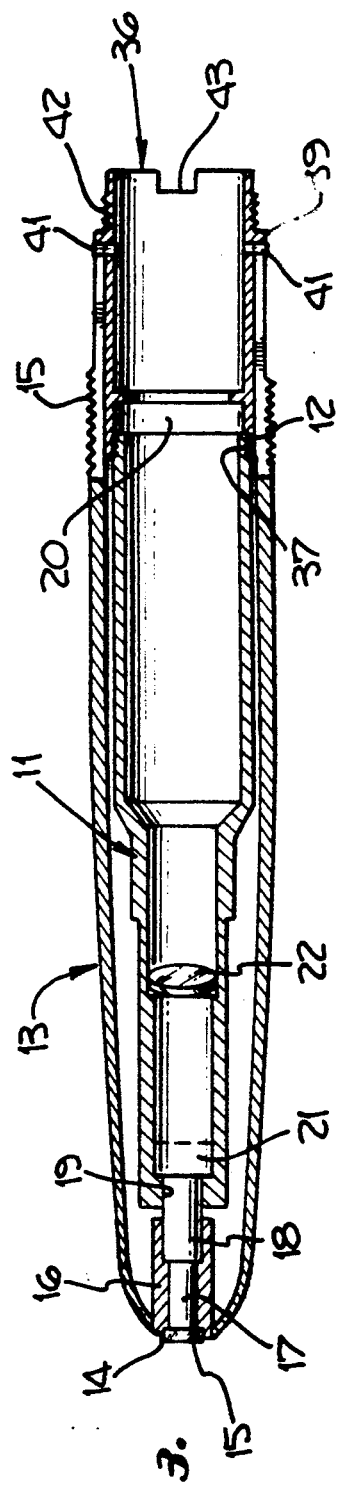

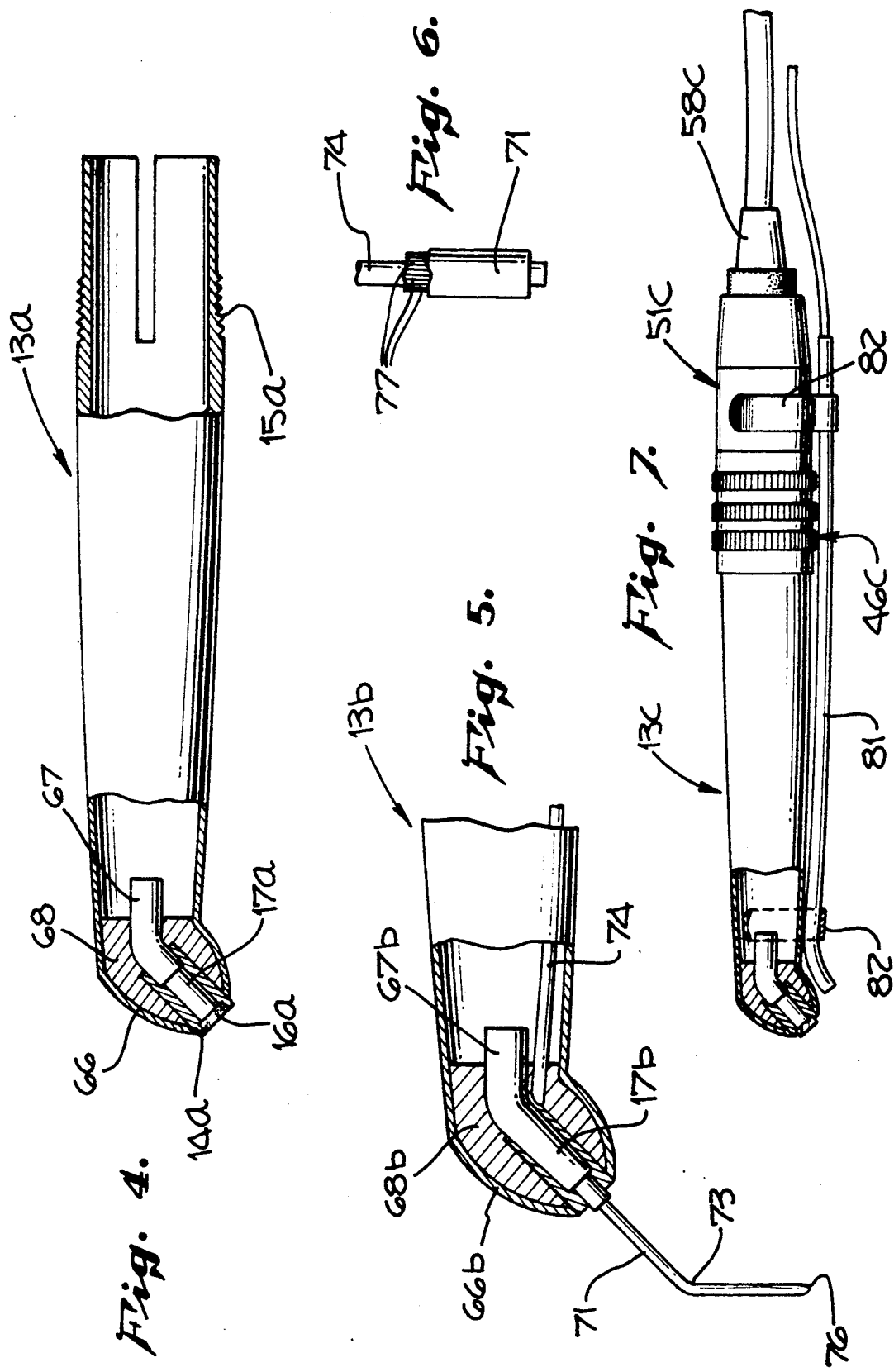

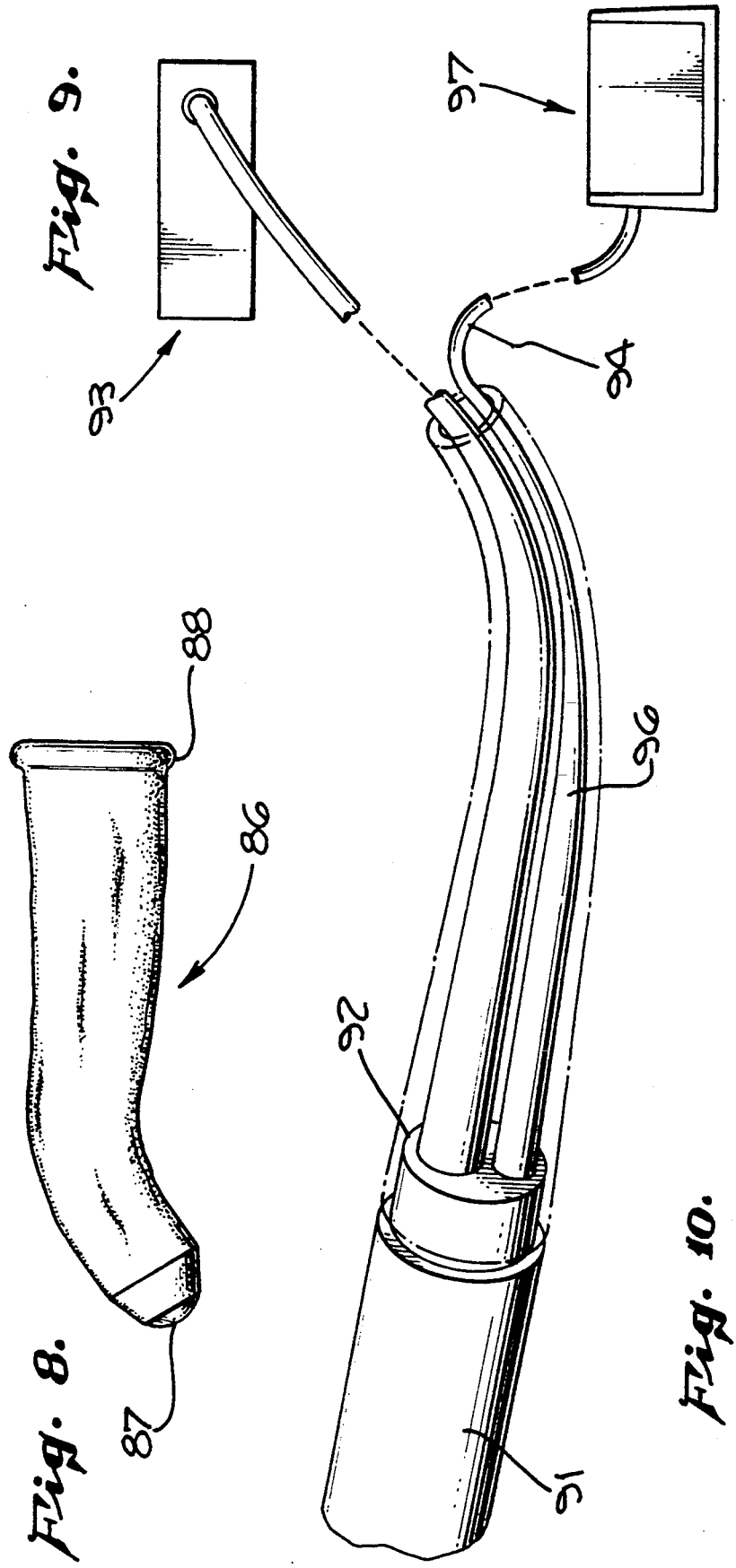

MODULAR VIEW LENS ATTACHMENT FOR MICRO VIDEO IMAGING CAMERA

BACKGROUND OF THE INVENTION

1. Field of the Invention

This invention relates to a new and improved modular view lens attachment for micro video imaging camera. Miniature cameras of this general type have been increasingly adopted in the dental and medical fields for diagnosis and for viewing during treatment. Typical uses are in the examination of teeth and specifically root canal dentistry and for examination of joints such as temporal mandibular joint examination.

2. Description of the Related Art

Miniature cameras of various types have been used for several years in this general field. One of the problems of such use, however, is that sterilization by autoclaving has not heretofore been practical. In accordance with the present invention the lens system on the distal end of the camera handpiece is detachable and is so constructed that it may be sterilized. Alternatively, a plastic sheath having a clear plastic tip may be slipped over the instrument to prevent cross-contamination of patients.

SUMMARY OF THE INVENTION

A module consisting of a body containing a magnifying lens, filter and a fiber optic image conduit is detachable from the proximal end of an instrument. This module encloses an inner body which comprises a lens tube containing a focusing lens. The module is detachable from a proximal housing which incorporates a charge coupled device (microprocessor) and video transmission components connected, in turn, to a video monitor. The distal module is sterilizable, whereas the proximal portion and inner body, which would not withstand autoclaving, do not require sterilization since they do not contact the patient.

Accordingly, a principal purpose of the invention is to incorporate in a single module the lens, filters, and fiber optics which may be detached from the other components of the system for interchange and for sterilization.

The lens at the distal end of the module may be axial (i.e., its field may be directly in line with the longitudinal axis of the module), or it may be angular relative to the major axis of the instrument.

A thin probe may be threaded into or otherwise attached to the distal end of the magnifying lens. Such a probe may have fiber optic light filaments surrounding the fiber optic lens in order to illuminate the field of view of the lens. It may also contain a laser transmitting quartz crystal and air and water ports.

Further features of the invention are the optional use of a tapered lens in the head of the module casing, a separate fiber optic light source clipped to the exterior of the casing, and a flexible, plastic sheath over the casing which has a clear plastic tip which does not interfere with the field of view.

BRIEF DESCRIPTION OF THE DRAWINGS

The accompanying drawings, which are incorporated in and form a part of this specification, illustrate embodiments of the invention and, together with the description, serve to explain the principles of the invention:

FIG. 1 is a side elevational view of an instrument in accordance with the present invention, the casing and lens system being broken away to reveal internal construction.

FIG. 2 is an exploded elevational view of the components of FIG. 1, some of these components being broken away to reveal internal construction.

FIG. 3 is an enlarged vertical sectional view through the lens body and its casing as well as the CCD body.

FIG. 4 is a view similar to FIG. 3 of an angular lens.

FIG. 5 is an enlarged sectional view through a modified lens having a probe secured thereto.

FIG. 6 is a fragmentary elevational view broken away in section to reveal internal construction of a portion of the probe of FIG. 5.

FIG. 7 is a side elevational view showing a fiber optic cable clipped to the exterior of the casing for the lens system.

FIG. 8 is a view of a sheath which may be slipped over the distal end of the instrument to eliminate the need for sterilization between uses.

FIG. 9 is a schematic perspective view showing connection of the proximal end of the cable to a charge coupled unit.

FIG. 10 is an exploded elevational view of a fiber optics cable and light source.

FIG. 11 is a sectional view of a lens head.

DETAILED DESCRIPTION OF THE PREFERRED EMBODIMENTS

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications and equivalents, which may be included within the spirit and scope of the invention as defined by the appended claims.

Directing attention to the modifications of FIGS. 1-3, an inner lens body 11 formed of aluminum or plastic is generally forwardly tapering and has external threads 12 at its proximal end. Inner lens body 11 is received within modular outer lens body 13 (see FIG. 3) which has a distal axial opening 14. Fitting in opening 14 is lens tip 16 which optionally may have a light filter 15 at its end to eliminate certain wave lengths of light. Behind filter 15 is a cylindrical magnifying lens 17 attached to image conduit optical segment 18. Distal opening 19 is formed in inner lens body 11 and the proximal end of image conduit optical segment 18 fits through opening 19.

In the body 11, immediately proximal of opening 19 is an optional distal filter 21. Optionally, the proximal end may be formed with counterbore 20 to receive a laser filter (not shown). Lens 22 is located in the inner body 11 in such position that it focuses the image received by image conduit optical segment 18 onto a microprocessor 27 hereinafter described.

Cylindrical Charge Couple Device housing 26 shown in FIG. 2 has a microprocessor 27 on its distal end which, in the assembled position of the instrument, is located so that the image focused by lens 22 is displayed on the face thereof. Housing 26 has a detachable modular plug 28 on its proximal end. Approximately midway of its length is an external sleeve 29 having forward projecting diametrically opposed tongues 31. Near its proximal end the housing 26 has a rubber ring 32 for sealing purposes and located within the housing 26 is a video transmitter shown generally by a reference numeral 33. It will be understood that the details of the transmitter 33 form no part of the present invention and are not herein illustrated or described.

CCD body 36 receives the forward portion of CCD housing 26. The distal end 37 of sleeve-like body 36 is formed with internal threads which mate with threads 12 on the inner lens body 11. On the proximal end of body 36 is a collar 39 and immediately distally of collar 39 are diametrically opposed alignment pins 41. Rearward of collar 39 are external threads 42, which mate with threads 12 on inner body 11.

Fitting over the outside of the proximal end of CCD body 36 and CCD housing 26 is a retainer sleeve 46. Sleeve 46 has bands 47 (here shown as three in number) which are knurled or otherwise configured so that the user may grip and/or turn the retainer 46. The distal end of retainer 46 has internal threads 48 which mate with the proximal external threads 15 of outer lens body 13. The proximal end of retainer ring 46 is formed with a shoulder 49 which engages the collar 39 in the assembled condition of the instrument.

Rear body 51 comprises a ring having internal distal threads 52 which mate with the threads 42 of CCD body 36. Set screws 53 hold the CCD body 36 and rear body 51 fixed relative to each other. Shoulder 54 approximately midway of the interior of rear body 51 engages flange 32 in the assembled condition of the instrument. The open end 56 of rear body 51 accepts a modular plug 58 which engages the modular plug 28. A seal 59 seals the plug 58 to the rear body 51.

It will thus be seen that the retainer ring 46 permits swiveling of the parts so that the user is free to use the instrument without interference. The user grips the retainer 46 and maneuvers the tip 16 in such manner as to focus on the lens 22 the image to be observed, the lens 22 in turn focusing on the microprocessor chip 27 which through the video transmitter elements 33 are transmitted through the modular plugs 28–58 as shown in FIG. 9 and cable 91. Cable 91 may be enclosed in sheathing 92 and connected to a charge coupled unit 93. Sheathing 92 may also enclose a fiber optics cable 94 within a sheath 96 of stainless steel or the like which connects to a light source 97. The cable 94 may have a connector 98 (FIG. 11) intermediate its length having a wire coupling socket 99 at its proximal end a plug 101 fitting therein.

Body 13 may be disconnected by turning retainer 46 relative thereto, separating threads 15,48. Image conduit optical segment 18 is slipped out of opening 19. This permits body 13 to be sterilized or it may be replaced by other modular units such as the body 13a shown in FIG. 4. If desired, inner body 11 may be replaced merely by unscrewing threads 12, 37.

Directing attention to FIG. 4 which illustrates more or less schematically a 45° head lens (as distinguished from the 0° head lens of the preceding modification) the distal end 66 of outer lens body 13a is angularly disposed. Image conduit optical segment 67 is angled accordingly and is supported in position in the distal end 66 by support 68. The modular body 13a replaces body 13 of FIG. 3. Its proximal end is formed with opposed longitudinal slots which receive alignment pins 41 on CCD body 36 to align the angle of end 66 with microprocessor 27.

FIG. 5 illustrates a still further modification. A probe case 71 which is preferably of a material such as stainless steel or other readily sterilizable material, is formed on its proximal end with threads (not shown) which are threaded into an appropriate threaded hole (not shown) on the distal end of image conduit optical segment 67b. Hence the probe case 71 may be removed as desired in case it is damaged or a different probe case 71 having a different angled bend 73 is needed. Within the inner lens body 11b is a fiber optic light cable 74 connected at its proximal end to a light source 97 by connector 98. Located within the probe case 71 is a fiber optic lens 76 and this is preferably surrounded by fiber optic light filaments 77 which make up cable 74. Light from the filaments 77 illuminates the tip of the probe case 71. It will be understood by those skilled in the art that case 71 may contain in addition to filaments 77 a quartz crystal laser conduit and air and water conduits.

Probe case 71 may be removed and lens head 61 (see FIG. 11) slipped into opening 14. Head 61 may be angled (as shown in FIG. 11) or straight. It consists of an outer sheath 62 and inner bundle of fiber optic fibers 63 which connect to cable 74.

Instead of a light probe similar to that shown in FIGS. 5 and 6, as a substitute, shown in FIG. 7, a fiber optics cable 81 may be attached by clips 82 to the exterior of outer lens body 13c to illuminate the field of view of the instrument.

FIG. 8 shows a resilient, replaceable sheath 86 of polystyrene or other suitable material which may be slipped over the outer lens body 13. Sheath 86 has a clear plastic tip 87 which does not substantially reduce the amount of light accepted through the distal opening 14 of the probe of FIG. 1 or any of the other modifications of this invention. To secure the sheath 86 on the body 13, an O-ring 88 is encased on the proximal end of the sheath 86.

Many of the elements of the modifications of FIGS. 4, 5–6 and 7 resemble those of preceding modifications and the same reference numerals followed by subscripts a, b, and c, respectively, indicate corresponding parts.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. In a miniature video camera of the type having a proximal housing containing a CCD and video transmitter, the combination comprising:
    an inner body having a focusing lens therein formed with a distal opening and proximal attachment means to connect said inner body to the housing with said focusing lens focused on the CCD;
    a module comprising an outer body shaped to fit around said inner body, a distal magnifying lens for receiving an image through an open distal end of said outer body, and an image conduit optical segment fixed in said inner body to receive the output of said magnifying lens, said image conduit optical segment fitting into the distal opening in said inner body and transmitting light to said focusing lens;

a sleeve-like CCD body receiving the distal end of the proximal CCD housing, including first locating means for orienting the proximal CCD housing relative to said CCD body and second locating means for orienting said CCD body relative to said inner body;

a retainer ring surrounding said CCD body;

first cooperating means connecting the proximal end of said outer body to the distal end of said retainer ring;

a hollow rear body for receiving the proximal end of said CCD body; and second cooperating means connecting the proximal end of said CCD housing to the distal end of said rear body.

2. A camera according to claim 1 which further comprises cooperable means on said outer body and said CCD body to align said open distal end of said outer body relative to said CCD body.

* * * * *